United States Patent
Levenson et al.

(10) Patent No.: US 6,750,964 B2
(45) Date of Patent: *Jun. 15, 2004

(54) SPECTRAL IMAGING METHODS AND SYSTEMS

(75) Inventors: Richard Levenson, Brookline, MA (US); Peter J. Miller, Newburyport, MA (US)

(73) Assignee: Cambridge Research and Instrumentation, Inc., Woburn, MA (US)

( * ) Notice: Subject to any disclaimer, the term of this patent is extended or adjusted under 35 U.S.C. 154(b) by 13 days.

This patent is subject to a terminal disclaimer.

(21) Appl. No.: 10/183,335

(22) Filed: Jun. 25, 2002

(65) Prior Publication Data

US 2003/0030801 A1 Feb. 13, 2003

Related U.S. Application Data

(63) Continuation-in-part of application No. 09/921,040, filed on Aug. 2, 2001, now Pat. No. 6,690,466, which is a continuation of application No. 09/633,417, filed on Aug. 7, 2000, now Pat. No. 6,373,568.

(60) Provisional application No. 60/300,696, filed on Jun. 25, 2001, and provisional application No. 60/147,636, filed on Aug. 6, 1999.

(51) Int. Cl.$^7$ .................................................. G01J 3/28
(52) U.S. Cl. ...................................................... 356/326
(58) Field of Search .................................. 356/326, 328

(56) References Cited

U.S. PATENT DOCUMENTS

| | | | |
|---|---|---|---|
| 4,379,233 A | 4/1983 | Rosenthal | |
| 4,519,707 A | 5/1985 | Kuffer | |
| 4,669,878 A | 6/1987 | Meier | |
| 4,800,279 A | 1/1989 | Hieftje et al. | |

(List continued on next page.)

FOREIGN PATENT DOCUMENTS

WO WO 01/11343 2/2001

OTHER PUBLICATIONS

W.C. Sweatt et al., "ISIS; An Information–Efficient Spectral Imaging System," Imaging Spectrometry IV, Proc. SPIE, vol. 3438, pp. 98–106, San Diego, 1998.

B.R. Stallard, Construction of Filter Vectors for the Information–Efficient Spectral Imaging Sensor, Imaging Spectroscopy IV, Proc. SPIE, vol. 3438, pp. 172–182, San Diego, 1998.

L.O. Jimenez et al., "High Dimensional Feature Reduction via Projection Pursuit," TR–ECE 96–5, School of Electrical Engineering, Purdue University, West Lafayette, IN 47907–1285, Apr., 1995.

Hyvarien et al., "Novel Spectroscopic Techniques for Biomedical Applications," Optoelectronics Laboratory, Finland, SPIE vol. 2084, pp. 224–230.

Keraanen et al., "Thirty–two Channel LED Array Spectrometer Module with Compact Optomechanical Construction," Technical Research Centre of Finland, Electronics Laboratory, Finland, SPIE vol. 1533 Optomechanics and Dimensional Stability (1991), pp. 122–128.

Gentry et al., Biomedical Applications of the Information-–Efficient Spectral Imaging Sensor (ISIS), Gentry, SPIE vol. 3603, pp. 129–142.

(List continued on next page.)

*Primary Examiner*—Zandra V. Smith
(74) *Attorney, Agent, or Firm*—Fish & Richardson P.C.

(57) ABSTRACT

A imaging method is described that includes: obtaining a spectral weighting function indicative of an attribute of the reference sample; illuminating a target sample with light whose spectral flux distribution corresponds to the spectral weighting function to produce a corresponding target image, wherein the target image is indicative of a response of the target sample to the corresponding illumination at multiple spatial locations of the target sample; and identifying one or more target features in the target sample based on the target image.

27 Claims, 8 Drawing Sheets

U.S. PATENT DOCUMENTS

| | | | |
|---|---|---|---|
| 5,029,245 | A | 7/1991 | Keranen et al. |
| 5,042,893 | A | 8/1991 | Ong |
| 5,066,124 | A | 11/1991 | Wulf |
| 5,137,364 | A | 8/1992 | McCarthy |
| 5,424,545 | A | 6/1995 | Block et al. |
| 5,433,197 | A | 7/1995 | Stark |
| 5,539,517 | A | 7/1996 | Cabib et al. |
| 5,567,937 | A | 10/1996 | Pinkus |
| 5,608,213 | A | 3/1997 | Pinkus et al. |
| 5,719,024 | A | 2/1998 | Cabib et al. |
| 5,760,407 | A | 6/1998 | Margosiak et al. |
| 5,838,451 | A | 11/1998 | McCarthy |
| 5,912,165 | A | 6/1999 | Cabib et al. |
| 5,991,028 | A | 11/1999 | Cabib et al. |
| 5,995,645 | A | 11/1999 | Soenksen et al. |
| 6,007,996 | A | 12/1999 | McNamara et al. |
| 6,075,595 | A | 6/2000 | Malinen |
| 6,142,629 | A | 11/2000 | Adel et al. |
| 6,160,618 | A | 12/2000 | Garner |
| 6,373,568 | B1 * | 4/2002 | Miller et al. ................ 356/326 |

OTHER PUBLICATIONS

Shnitser et al., "Spectrally Adaptive Light Filtering," Physical Optics Corporation, Torrance, CA, SPIE vol. 3140, pp. 117–127.

Stallard et al., "Construction of Filter Vectors for the Information–Efficient Spectral Imaging Sensor," Sandia National Laboratories, Albuquerque, NM, SPIE vol. 3438, pp. 172–182.

Sweatt et al., "ISIS: An Information–Efficient Spectral Imaging System," Sandia National Laboratories, Albuquerque, NM, SPIE Vo. 3438, pp. 98–106.

Jimenez et al., "Supervised Classification in High Dimensional Space: Geometrical, Statistical and Asymptotical Properties of Multivariate Data," IEEE Transactions on Geoscience and Remote Sensing, vol. 37, No. 6, Nov. 1999; Project in Pursuit in Hyperspectral Data Analysis, Jimenez & Landgrebe, Nov. 23, 1999, pp. 1–32.

* cited by examiner

SPECTRAL IMAGING METHODS AND SYSTEMS

CROSS-REFERENCE TO RELATED APPLICATIONS

This application claims priority to, and is a continuation-in-part of, U.S. utility patent application Ser. No. 09/921,040, entitled "Spectral Imaging System" by Peter J. Miller and C. Hoyt, and filed Aug. 2, 2001 now U.S. Pat. No. 6,690,466, which is a continuation of U.S. utility application Ser. No. 09/633,417, entitled "Spectral Imaging System" by Peter J. Miller and C. Hoyt, and filed Aug. 7, 2000 now U.S. Pat. No. 6,373,568, which claimed priority to provisional application Ser. No. 60/147,636, entitled "Spectral Imaging System" by Peter J. Miller and C. Hoyt, and filed Aug. 6, 1999. This application also claims priority from U.S. provisional patent application Serial No. 60/300,696, entitled "Spectral Imaging Systems and Methods" by Richard Levenson, and filed Jun. 25, 2001. The contents of these utility and provisional patent applications are incorporated herein by reference.

BACKGROUND

Advances in the molecular understanding of many diseases and conditions depend, to a large extent, on microscopic evaluation of tissues. For example, malignant cells are identified by evaluating tissue samples. It is one of the most arduous and time-consuming tasks in pathology. To facilitate the evaluation, tissue samples can be treated with stains to provide feature contrast.

Human color vision is a form of spectral imaging by which we determine the intensity and proportion of wavelengths present in our environment, and their spatial distribution. However, unlike the eye, which breaks up the light content of an image into red, green, and blue, instrument-assisted spectral imaging can use an arbitrarily large number of wavelength-classes. Furthermore, it can extend the range to include the ultraviolet and infrared regions of the spectrum invisible to the unaided eye. The result of spectral imaging is a data set (known as a data cube) in which spectral information is present at every picture-element (pixel) of a digitally acquired image.

SUMMARY

The invention features a method that forms one or more images of an unknown sample by illuminating the sample with a weighted spectral distribution for each image. The method analyzes the one or more resulting images and identifies target features. The identifying can include classifying regions of the images based on their spectral or/and spatial properties. In addition to classifying, the method can quantify the amount of some biomarkers either in combination or apart from the classifying. The identification of particular target features can guide the automation of subsequent processes.

In general, in one aspect, the invention features a method for imaging. The method includes: obtaining a spectral weighting function indicative of an attribute of the reference sample; illuminating a target sample with light whose spectral flux distribution corresponds to the spectral weighting function to produce a corresponding target image, wherein the target image is indicative of a response of the target sample to the corresponding illumination at multiple spatial locations of the target sample; and identifying one or more target features in the target sample based on the target image.

Embodiments of the method may include any of the following features.

The spectral weighting function may be obtained from a set of reference images. The spectral weighting function may be determined based on at least one of principal component analysis, projection pursuit, independent component analysis, convex-hull analysis, and machine learning The method may also include illuminating a reference sample at each of a plurality of pure spectral bands to produce the set of reference images, wherein each reference image is indicative of a response of the reference sample to the corresponding illumination at multiple spatial locations of the reference sample.

The method may also include determining one or more additional spectral weighting functions indicative of additional attributes of the reference sample based on the set of reference images; and illuminating a target sample with light whose spectral flux distribution corresponds to each of the additional spectral weighting functions to produce additional corresponding target images, wherein each target image is indicative of a response of the target sample to the corresponding illumination at the multiple spatial locations of the target sample. The response of the reference sample may include transmission, reflectance, or fluorescence. The response of the target sample may include transmission, reflectance, or fluorescence. The spectral weighting function may include multiple ones of the spectral bands. The spectral weighting function is a single one of the spectral bands.

The method may include preparing the reference and target samples with markers suitable for chromogenic in-situ hybridization. The response of the target sample to the spectral weighting function may correlate with the presence of the in-situ hybridization marker in the target sample. The method may include preparing the reference and target samples with a marker suitable for color immunohistochemistry. The response of the target sample to the spectral weighting function correlates with the presence of the color immunohistochemistry marker in the target sample. The method may include preparing the first reference and first target with a general stain.

The identification may include assigning the one or more target features to one or more classes. The identification may include quantifying the amount of a chromogen in a target feature.

The method may further include automating a subsequent process based on the identification of the one or more target features. The subsequent process may include laser capture microdissection. The laser capture microdissection may include directing laser energy to the identified target features in the target sample to remove corresponding portions of the target sample. The method may include performing mass spectroscopy on the portions of the target sample removed by laser capture microdissection process. The mass spectroscopy may be protein mass spectroscopy. The may also include performing protein purification on the portions of the target sample removed by laser capture microdissection process. The subsequent process may include determining the extent of a condition or disease in a target sample. The condition may be fibrosis. The condition may be chronic organ rejection The method may also include repetitively illuminating the target sample with light whose spectral flux distribution corresponds to the spectral weighting function to record the target image as a function of time. The identifying one or more target features may be based on the time dependence of the target image.

This application incorporates other documents by reference. In case of conflict, this document controls.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

The invention features a method for recording images of an unknown sample and identifying target features in the unknown image. Although the method finds use in many applications, it is particularly useful in the field of biological tissue examination.

Figure 1:
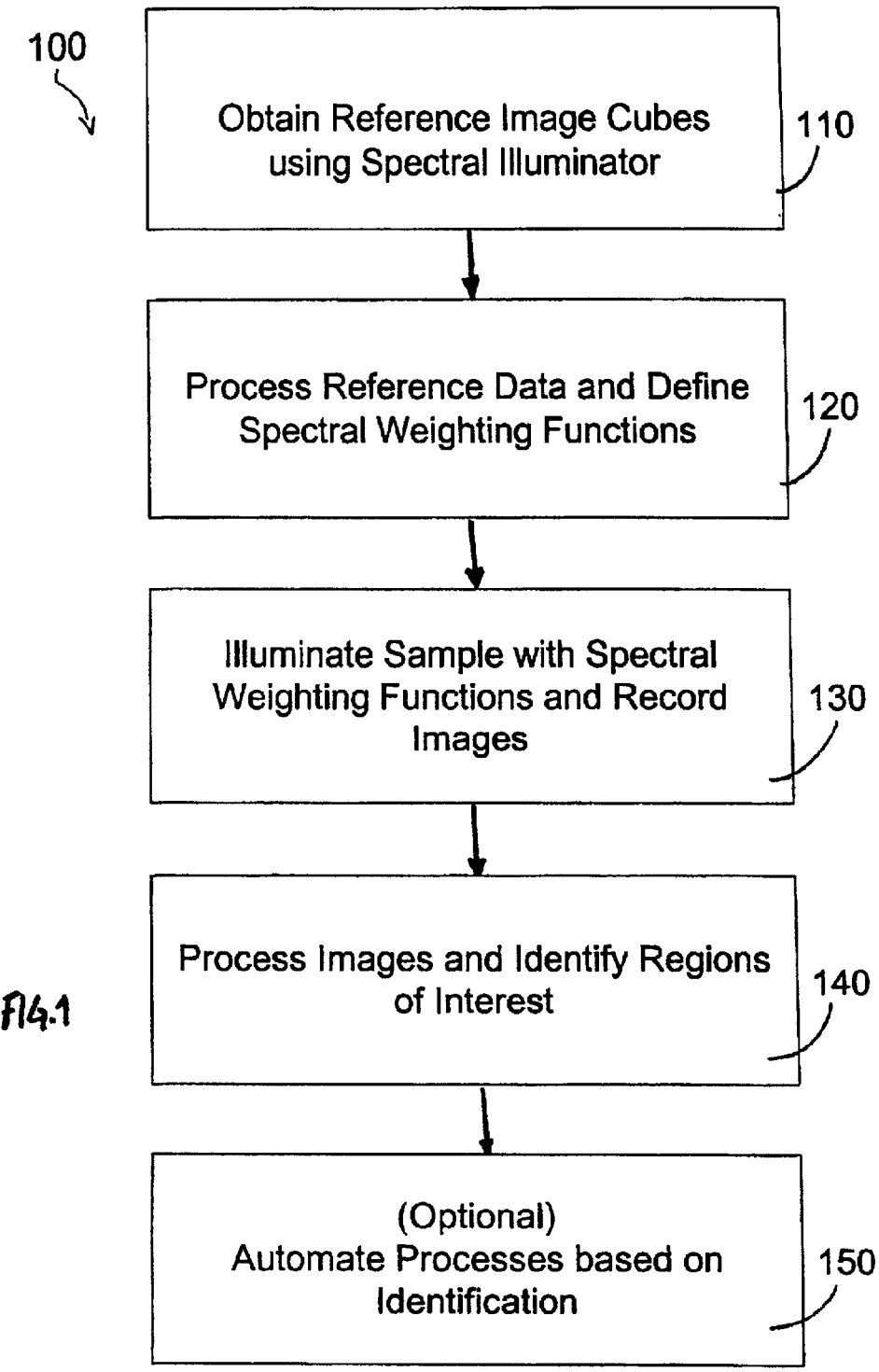
FIG. 1 is a flow chart of a method for using a spectral illumination system to analyze a sample.

A method 100 for identifying target features from one or more images of an unknown sample is outlined in the flowchart of FIG. 1. Referring to FIG. 1, method 100 begins by recording one or more reference image cubes from one or more reference samples (Step 110). An image cube is the spectral response of the sample as a function of spatial position and wavelength. If the goal were to assign target features to two classes (for example disease vs normal cells) then representative image cubes would be recorded for both classes. In other applications, if the goal were to quantify the amount of some biomarker such as those in used immunohistochemistry, then the reference samples would include a sample with the pure immunohistochemical biomarker. Using standard techniques, these reference image cubes form a training set. The training set is then processed to define one or more spectral weighting functions (Step 120). A spectral weighting function is the weighted sum of the spectral response at various spectral bands. The spectral weighting functions are determined to be functions whose values are particularly relevant in identifying the target features. Once the spectral weighting functions are defined the spectral illuminator illuminates the sample with a flux distribution equal to the light distribution of the spectral weighting function (Step 130) and the light intensity recorded by a detector is the spectral weighting function. The resulting images are processed to identify the target features. The identification is based on a comparison between the images of the unknown sample and the training set (Step 140). Once the target features in the sample have been identified, subsequent tasks can be automated based on the identification (Step 150).

The method is suitable for the analysis of biological tissue samples. In the following, we describe examples of techniques for preparing such biological tissue samples. To enhance the visibility of features, staining can be used to improve contrast in such tissue samples. For example, fixed slices of tissue can be stained with hematoxylin and eosin (H&E). Because these dyes have certain affinities for cellular constituents they enhance contrast and visibility of cellular features. There also other stains that are suitable for use with method 100. For example, cytopathology specimens, including cervico-vaginal "Pap" smears, can be stained with other dyes, including the Romanowsky-Giemsa formulation (azure B and eosin Y) and the Papanicolaou stain (hematoxylin, orange G eosin Y and light green). Other suitable stains include toluidine and methylene blue.

In addition to staining specific cellular features, conditions such as inflammation and neoplasia and other physiological and pathological processes affect the distribution, intensity and color of the stains. Thus the overall spectral signature of such stains is characteristic of the various cellular components and further detailed spectral analysis can diagnose subtle physiological and pathological changes. For example, by analyzing the image cubes of stained specimens, neoplastic vs. normal cells of the same cellular lineage can be distinguished and classified.

Such general stains typically bind non-specifically. For example, hematoxylin, a blue dye, stains predominantly nuclear features whereas eosin stains cytoplasmic and extracellular components pink-red. Classifying target features using such general stains is based on empirical information. The method forms a training set of known samples that have been stained with such general stains. Typically, the known samples include representative samples for each class that may later be identified.

In contrast to the general staining methods, other techniques such as histochemical staining generally involve a previously established binding mechanism. For example, histochemical stains can be directed specifically at cellular constituents such as elastin or collagen. Typically, these methods employ chemical reactions targeted at different biochemical species in tissue and generate a color signal via various mechanisms. Such techniques can be used to identify specific structures; constituents and cell types and can also be used to provide quantitative information. The method first obtains spectral information about the tinctorial properties of the various components in a sample, and uses this spectral information to identify and quantitate such components.

Another suitable technique for marking specific features with chromogens is immunohistochemistry (IHC). IHC is the detection of antigens using antibodies that are coupled to some kind of chromogenic readout system. Immunohistochemistry provides a very high level of specificity in its binding due to the highly specific interaction between antibody and antigen. For example, an suitable sample preparation using IHC includes a brown chromagen (DAB) to an immunostain that recognzies the progesterone recepter and red chromagen (Fast Red) coupled to a immunostain recognizing the estrogen receptor. The levels of the chromogenic markers used in IHC can be used to measure quantitatively the levels of estrogen- and progesterone-receptors. Similar sample methods can quantitatively measure the levels of other important biological targets such as Her2-neu expression, p53, and ki-67.

In situ hybridization (ISH) is the specific tagging of nucleic acid sequences with a chromogenic readout system.

Non-fading, enzyme cytochemical detection methods for hybridization sites have been developed and have led to chromogenic in situ hybridization. Typcial ISH probes include centromeric markers, telomeric markers, subtelomeric markers, single gene markers as well as mutation, deletion, amplification and rearragement detection systems. In a fashion similar to IHC, chromogenic ISH provides highly specific information due to the specificity of the hybridization. An example of samples labeled using ISH include bladder carcinoma tissue sections hybridized with centromeric chromosome I probe coupled to biotin or dioxigenin and visualized using DAB or HPR-TMB respectively.

Combining these various techniques simultaneously can produce an especially information rich composite probe of tissues. For example, chromogenic ISH can be combined with IHC to provide multiparameter molecular characterization of cancer biology. In such settings, the method 100 is well suited to analyzing images of samples that have been treated with such composite probes.

In what follows we first describe a spectral illumination system especially suited for implementing the method. This is followed by an expanded description of method 100. Thereafter, we describe alternate embodiments of the spectrally illuminator and we describe the spectral illumination system electronics.

Figure 2:
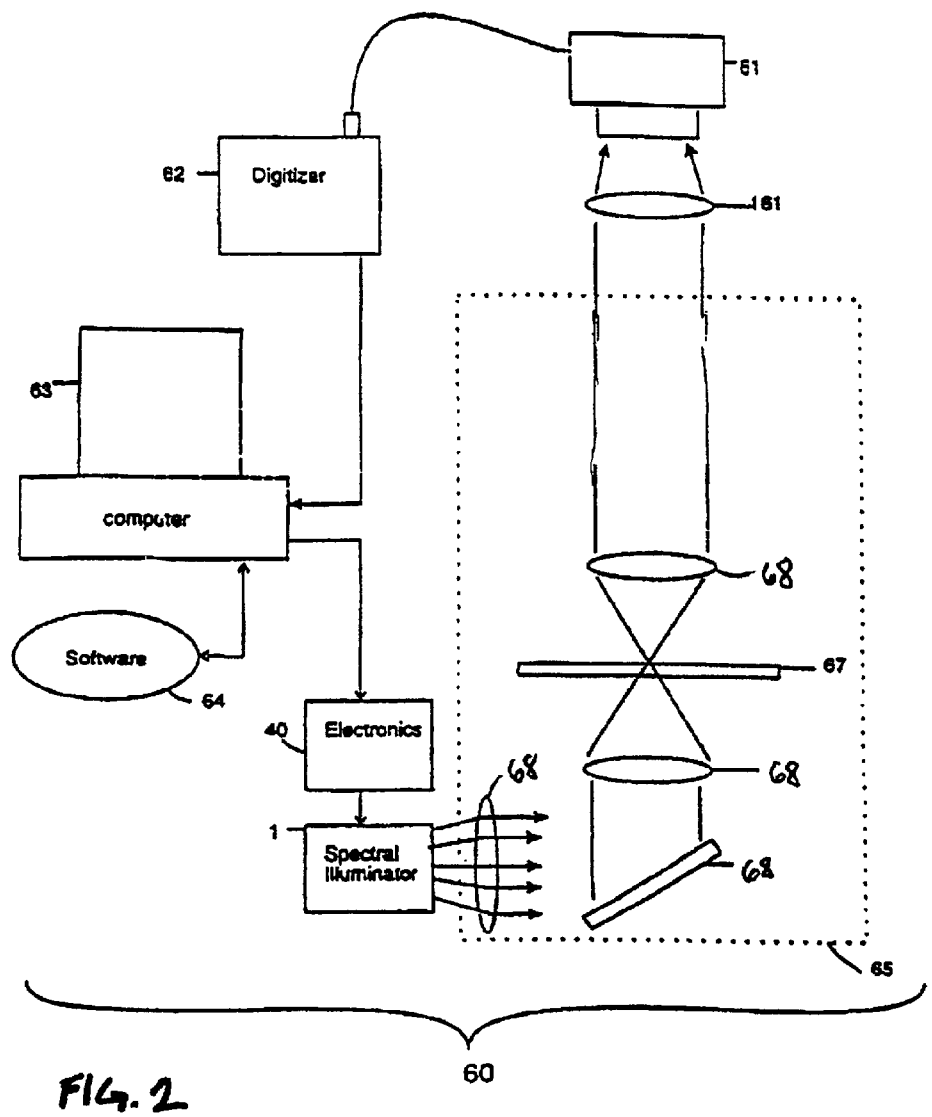
FIG. 2 shows a spectral illumination system for spectral measurements of a sample on a microscope slide.

A system for making spectral image measurements is illustrated in FIG. 2. A spectral illumination system 60 includes a spectral illuminator 1 driven by electronics 40 and controlled by computer 63. The spectral illuminator is controlled to provide light output, $I(\lambda)$, that can be independently varied for bands of wavelength for any band in the illuminator bandwidth. Typically the bandwidth is centered in the visible spectrum. The spectral illuminator is described in detail below. A spectral illuminator is suitable, so long as it provides a plurality of well-defined bands with minimal overlap that span the spectral ranges of interest. The flux from each band is adjustable and reasonably reproducible, and multiple bands can be active at one time.

The light output of the illuminator is directed into microscope 65. The optical elements 68 of the microscope guide the light toward the sample 67 and from the sample towards detector 61. The light illuminates sample 67 and the transmitted light is directed to detector 61 via lens 161. The detector collects an image of the sample. The signal from the detector is digitized by digitizer 62 and is transferred to computer 63. The control of the spectral illuminator and the processing of the resulting images are performed by instructions from software 64.

The system shown in FIG. 2 is suitable for obtaining transmission images using a microscope. In other embodiments, the system can measure reflectance, scattering, or even fluorescence. Furthermore, the system may use microscope imaging technqiues or macro-scopic imaging techniques.

In general, the signal induced at a detector by light in an infinitesimal spectral band centered at $\lambda_0$ and having width $d\lambda$ will be given by $$D(\lambda_0)=I(\lambda_0)\ S(\lambda_0)\ R(\lambda_0)\ d\lambda \qquad [1]$$

where D is the signal produced at the detector, I is the illumination flux, S is the spectral response of the sample, and R is the detector responsive for the given wavelength.

S may indicate reflection, transmission or scatter, depending on how the sample is being illuminated and viewed, (i.e. by a transmissive, reflective, or scattering arrangement). In the present context, these are all equivalent so long as the wavelength of light is substantially unaltered by its interaction with the sample.

It is possible to rewrite the Eq. [1] in terms of discrete bands, provided that the bands are chosen to be sufficiently narrow that neither the illumination, sample response, nor detector response varies greatly within a given band. Then one may write the expression for the contribution from light in the j-th band as $$D(j)=I(j)\ S(j)\ R(j)\ d\lambda j \qquad [2]$$

One normalizes spectral readings against a standard such as a white card (for reflection measurements) or a transparent reference (for transmission measurements). This normalization is performed on a band-by-band basis, and typically for the standard $S(\lambda)=1$, leading to a signal of $$D(j)=I(j)\ R(j)\ d\lambda j \qquad [3]$$

when the standard is read. This allows one to measure the normalized sample property S(j) by taking the ratio of the detector readings when the sample is present, relative to when the standard is present, as:

$$S(j)\text{measured}=D(j)\text{sample}/D(j)\text{standard}=I(j)\ S(j)\ R(j)\ d\lambda j/I(j)\ R(j)\ d\lambda j=S(j) \qquad [4]$$

It is this same method that is used to determine the image cube for a sample. One illuminates with each wavelength band in turn and observes the detector reading D(j), under both sample and standard conditions for every pixel in the image plane; the ratio yields the sample response S(j) which when measured for each pixel r in the image plane becomes the image cube S(r,j).

As was described above, the method identifies target features in images of an unknown sample (or samples) and that identification relies on the reference images. The reference images depend on the type of identification that is to be performed by the method. For example, for classification based on samples prepared with nonspecific general staining, the reference images are representative of each class that is to be identified in the image. For example, if normal cells are to be distinguished from diseased cells then representative samples of diseased and normal cells are obtained that have been stained using the protocols used for the unknown samples. From the resulting training set, the method assigns features in the images of the unknown sample based on the training set. Programmable, reliable automated staining systems are available from Ventana Medical Systems (Tucson, Ariz.).

For chromogen quantification, the reference samples provide the spectral information about the chromogen of interest. As the actual sample can be stained using a combination of the techniques described above, the quantification of a single chromogen often requires spectral information about each of the chromogens present in the sample so that the contribution of the chromogen of interest can be unmixed from the others.

For preparation of IHC based biomakers, techniques can use enzyme-based color generation systems, usually coupled with other amplification schemes. Two enzymes are commonly used for this purpose, alkaline phosphatase and horseradish peroxidase, each of which can catalyze the deposition of colored precipitates in their vicinity.

For preparation of ISH based markers, a number of suitable enzymes for ISH detection procedures are now commercially available. For example, ISH markers are available from Zymed Laboratories Inc. (South San Francisco, Calif.). The best results have been obtained with horseradish peroxidase and alkaline phosphatase. To obtain 3- or more color results, it is possible to quench residual enzyme activity from the first rounds of chromogen deposition and then come back with other enzyme-linked probes using a different set of chromogens. For example, HRP-DAB (brown), HRP-TMP (blue-green) and AP-fast red or new fuchsin can be combined. In some embodiments, catalyzed reporter deposition (CARD) using tyramide conjugates is used.

The first step of method 100 uses the spectral illumination system 1 to obtain reference image cubes from reference samples. Typically these reference samples are prepared using one or more of the techniques described above (general staining, hsitochemistry, IHC, chromogenic ISH). The reference samples are chosen based on the type of features that are to be identified. In addition similar protocols are followed for both the reference samples as will be used for the unknown sample. This ensures that variability in the spectral features due to lot-to-lot changes in the stains or other systematic errors can be minimized. Some embodiments prepare the reference samples at separate times than the unknown samples. In yet other embodiments the spectral cubes of interest are obtained from other sources such as reference sources for spectral information about stains or chromogens. Such choices are determined by the application at hand.

As described above, the spectral illuminator 1 can sequentially illuminate the reference sample(s) band by band while recording the spectral response of the sample for each band. This data set forms the image cube. The one or more image cubes of the one or more reference samples provide the raw data sets also known as the training sets that are later used in identifying target features.

Once the image cubes are obtained for the reference samples, computer 63 processes the input raw image cubes of the reference samples and derives the spectral weighting functions from the reference image cubes (Step 120).

The spectral weighting function WF and its distribution F(j) are derived from the image cubes using methods that are familiar to one skilled in the art of spectroscopy and multispectral image analysis. Given a spectral weighting function with a spectral distribution F(j) for a specified set of bands λj, the spectral index for a sample with response S(j) is given by:

$$WF = \text{sum } [S(j) \, F(j) \, d\lambda j] \quad [5]$$

The distributions F(j) are chosen such that the weighting function WF of an unknown sample is the basis for identifying the features of interest in the unknown image. For example, when the goal is to assign target features to various classes, then the spectral weighting functions are chosen to optimize class separation. Often standard statistical tools are employed to analyze the training set data and the spectral weighting function and the subsequent target feature classification (see discussion of step 140 below) uses the information derived from such statistical analysis. When the goal is to quantitatively determine the amount of a chromogen, then the spectral weighting functions are chosen such that pixel-unmixing algorithms can extract and compute the amount of chromogen present in the spectral data from the unknown sample.

Techniques to derive the spectral weighting functions are described in the prior art such as "ISIS; An Information-Efficient Spectral Imaging System", by W. C. Sweatt, C. A. Boye, S. M. Gentry, M. R. Descour, B. R. Stallard, C. L. Grotbeck, Imaging Spectrometry IV, M. R. Descour, S. S. Shen Ed., Proc. SPIE, Vol. 3438, pp. 98–106, San Diego, 1998; "Construction of filter vectors for the Information-efficient Spectral Imaging Sensor", by B. R. Stallard, , S. M. Gentry, Imaging Spectrometry IV, M. R. Descour, S. S. Shen Ed., Proc. SPIE, Vol. 3438, pp. 172–182, San Diego, 1998; "Spectrally Adaptive Light Filtering", by P. I. Shnitser, I. P. Agurok, Proc. SPIE, vol. 3140, p.117–27, 1997; "High Dimensional Feature Reduction via Projection Pursuit", by L. O. Jimenez,, D. Landgrebe, TR-ECE 96-5, School of Electrical Engineering, Purdue University, West Lafayette, Ind. 47907–1285, 1995; all of whose contents are incorporated by reference in their entirety.

One such technique is principal component analysis (PCA). PCA is a widely used tool in a broad range of disciplines in which multidimensional data are commonplace. In the context of spectral image analysis, PCA may best be viewed as a method seeking a linear transformation of the input spectral image that optimally approximates the latter in a least square sense. The individual principal components, which are the eigenvectors of the covariance matrix of the input image, are all uncorrelated and point in the directions of maximal variance of the data points. In this way, PCA achieves what is sometimes called a faithful representation of the input data. PCA is useful in computing spectral weighting function that optimizes separation between classes.

Since PCA is exclusively based on the second-order statistics contained in the covariance matrix, it will fail to detect any higher-order structure, i.e., relationships between more than just two pixels, in the input data. Traditionally, this limitation has not received much attention because input data were generally assumed to conform to some approximation to a Gaussian distribution and for the particular case of Gaussian input data it can be shown that indeed all information is captured in the covariance matrix.

Another technique, independent component analysis (ICA) uses image transformations that explicitly incorporate higher-order statistics to obtain a meaningful representation of the image data. This is a much stricter requirement than mere uncorrelatedness of the PCA components. Only in the case of Gaussian input data, the implicit assumption of PCA, uncorrelatedness of the components is already sufficient for independence. Intuitively, ICA can therefore be understood as a linear transformation that maximizes non-Gaussianity rather than variance. A useful approach is actually to apply PCA operations prior to ICA.

Another technique is projection pursuit (PP). Often PP is used to compute spectral weighting functions that are useful for spectral unmixing. In PP, a projection index is used to find projections in multivariate data that are structured in a non-random and therefore "interesting" way. Since in most applications the Gaussian distribution is considered the least interesting (and most projection indices used in PP are indeed some measure of non-Gaussianity) the ICA components are in fact special variants of PP axes.

The type of identification that is to be performed also determines the number of spectral weighting functions that are computed. As the number of classes increases, typically the number of spectral weighting functions needed to accurately classify objects increases. Similarly when quantifying a chromogen from amongst an increasing number of overlapping stains, the number of spectral weighting functions necessary to accurately unmix and quantify that chromogen increases.

Sometimes an optimum spectral weighting function may correspond to one of the pure spectral tones, see, e.g., commonly owned U.S. Provisional Application Ser. No. 60/314,367 by Paul Cronin et al., filed Aug. 23, 2001 and entitled "Multispectral Imaging Method and Apparatus," the contents of which are incorporated herein by reference.

Once the spectral weighting functions have been determined, the spectral illumination system uses the spectral weighting functions to image the unknown sample 67. The computer 63 adjusts the settings of the universal spectral illuminator to produce an illumination spectrum with the property that $$I(j)=F(j)/D(j) \quad [6]$$

That is, the illumination distribution has the shape of the spectral weighting distribution F(j), divided by the detector responsivity D(j). The spectral weighting functions can be a single band in the spectral illuminator, or they can include multiple bands.

When the sample is imaged under this controlled illumination, the total signal at the detector D is given by $$D=\text{sum } [I(j) \ S(j) \ D(j) \ d\lambda j]=\text{sum } [F(j)/D(j)*S(j)*D(j) \ d\lambda j]=\text{sum } [S(j) \ F(j) \ d\lambda j]=WF. \quad [7]$$

The detector directly measures the value of the spectral weighting function, without need for breaking the light up into its constituent spectrum and numerically analyzing it. The result is an optical, rather than numerical, evaluation of the spectral weighting function, with enormous increase in speed and efficiency.

In spectral illuminators which use LED's, the LED current settings which realize the required illumination spectral distribution can be calculated directly from tabulated α(j) values; the proper LED current setting for band j is simply F(j)/α(j). The scale factors α(j) are found as follows. The LED output is variable, it is possible to adjust the LED current setting so as to attain a sought-for reading at the detector, which we denote as K. By doing so in all bands, and recording the drive current settings C(j) required to meet this condition, one can calculate a calibration table of scale factors α(j):

$$\alpha(j)=K/C(j) \quad [8]$$

The scale factor α(j) is the detector response per unit of LED drive current in band j.

The spectral illuminator is then set to produce the spectral distribution specified by the spectral weighting function, and an image of the entire sample is acquired. If several spectral measures are desired, then several exposures are taken. However, only one exposure is required for each spectral measure. Collecting the spectral weighting functions using this method is also known as matched filtering In some embodiments, the spectral illumination system will record multiple images of the spectral weighting functions as functions of time. Such a time series of data allows the calculation of the time evolution of the samples spectral properties.

Having collected the values of the spectral weighting functions from the sample, the images are processed and the target features are identified (Step 140). In the first step of the image processing, objects contained in the image scene are separated from the background (image segmentation). The method segments the image by locating the target features and removing the background. In some embodiments, the image is not segmented and each pixel in the image is classified or quantified. In addition to using spectral information for segmentation, spatial information can also be used.

Once the background is removed and the images have been segmented, the target features are identified. When assigning objects into classes, the method assigns the objects into classes based on the value of one or more of their spectral weighting function. As described above, such an assignment relation typically is based on a statistical analysis of the training set data.

There are several approaches to classifying pixels in a spectral image. The minimum squared error method compares each pixel in the image with a set of reference spectra using a least-squares criterion. Other approaches convert spectra into n-dimensional vectors, and the angles between such vectors can be used as measures of similarity. Pixels are classified according to which pure spectrum they are most similar to and can be pseudo-colored to indicate the results of classification. There are more advanced distance measures, such as Mahalanobis distance, which can take into account variations of signatures. Determining which spectra to use for the classification procedure is not always straightforward. In simple cases, the reference spectra can be selected from obvious structures in the image (foci of cancer vs. normal cells, for example) or from established spectral libraries. Alternatively, informative spectra can be extracted using statistical analysis methods, such as principal component analysis (PCA) or clustering methods. Instead of using a classified pseudo-color display, spectral similarity can also be illustrated by mapping the degree of similarity using gray-scale intensity.

In an exploratory context, the target classes as well as the features used for their subsequent discrimination have to be defined initially, typically in an iterative process: first, a set of preliminary target classes is defined, either manually under the guidance of an experienced pathologist or automatically by applying a clustering algorithm to the image data; second, the features that optimally discriminate between the target classes are selected; and third, the performance of the resulting classification system is evaluated by applying it to a new set of sample image data. If necessary, these three steps are repeated with different sets of preliminary target classes until satisfactory results are obtained.

The spectral classification methods are suitable for images in which no pure spectral components are likely to exist, such as in samples prepared with general stains. In other types of images, multiple distinct spectral signals may combine to form the detected signal. Spectrally mixed pixels result when objects cannot be resolved either at an object boundary (spatial mixture), or when more than one object is located along the optical path (depth mixture). A linear combinations algorithm can be used to unmix the signals arising from the pure spectral components. Given an appropriate set of standards, the algorithm can determine quantitatively the absolute amount of each label present. The linear combinations algorithm assumes each pixel is made up of a combination of pure spectra. Typically such a set of standards is provided by the training set.

$$s_{x,y} = Lw \quad [9]$$

$$s_{x,y} = \begin{bmatrix} L_{11} & \cdots & L_{1n} \\ \vdots & & \vdots \\ L_{m1} & \cdots & L_{mn} \end{bmatrix} \begin{bmatrix} w_1 \\ \vdots \\ w_m \end{bmatrix}$$

$S_{x,y}$ is a vector containing the spectrum at a pixel and L is a matrix with n pure spectra and m spectral channels. We solve the equation for w, which represents the contribution of each pure spectrum in L to a pixel $s_{x,y}$ in the image. The L matrix is overconstrained because there are usually more spectral channels than pure spectra. We must therefore find an approximation of w. Using the least squares approximation, we minimize the residuals e to give the best w.

$$e=\|Lw-s_{x,y}\|^2 \qquad [10]$$

We can determine quantitatively how much of each pure spectrum is in each pixel in the image using w. A grayscale image c is created for each pure spectrum in the library. Each pixel in each c image is assigned a fraction, according to w, of the total intensity of the corresponding pixel in the spectral image. We first normalize the weights w to w' so that the sum of all elements of w'=1. Let $I_{x,y}$ be the integrated density of the pixel at x,y. For each pure spectrum i=1 . . . n:

$$c_{x,y}^i = w'(i) I_{x,y} \qquad [11]$$

The linear combinations algorithm can only be applied in situations where the pure spectra combine linearly. This property holds for fluorescence images, but transmission and reflectance images must be converted to optical density before applying the linear combinations algorithm. Once the spectral unmixing algorithm determines the amounts of the pure spectra, the amount of the chromogen associated with the pure spectrum is computed.

In some embodiments, the analysis for identifying target features may also include morphology-based analysis. In order to provide such identification, the training sets are provided with representative images of the morphological types that are to be identified.

In yet other embodiments, both spectral and spatial image information are used to identify and classify the images. For example, an algorithm known as GENIE, a machine learning algorithm, uses both spectral and spatial information (See "GENIE: A Hybrid Genetic Algorithm for Feature Classification in Multi-Spectral Images", Simon Perkins, James Theiler, Steven P. Brumby, Neal R. Harvey, Reid B. Porter, John J. Szymanski, and Jeffrey J. Bloch Proc. SPIE 4120, pp 52–62, 2000). Other embodiments can use other machine learning algorithms or genetic learning algorithms.

With the results of feature identification subsequent tasks that depend on the outcome of that identification can be automated (Step 150). One such task is the automation of standard laser capture microdissection (LCM). Standard LCM is a method by which pure cell populations are selected by an expert operator from a heterogeneous sample that may contain many types of cells in addition to the target cell type. In the case of the PixCell LCM device (available from Arcturus, Mountain View, Calif.), laser "shots" are used to fuse a plastic film to the desired cells. This allows the separation of the selected cells from the unselected cells thus resulting in the pure population. Individual shots must be fired over and over again to pick up material. Standard LCM requires a large amount of user input and the process can be extremely tedious.

Often these pure cell populations produced by LCM are used as input material for protein identification and purification schemes in order to isolate and attain samples of the proteins being expressed by the pure cell populations.

By coupling the imaging and identification capabilities of the method 100 to a LCM device, the entire process can be automated. Images of samples containing mixed cell populations are segmented into spectrally homogeneous populations based on the reference images. The resultant segmented images can then be used to guide appropriate stage movements and laser actions in order to accomplish the microdissection procedure. The resulting pure cell populations can be fed directly into protein purfication or analysis systems such as protein mass spcetroscopy.

A number of other areas are suitable for automation. For example, the method can automate the quantification and extent of conditions or disease in tissue that has already been diagnosed. In conditions such as fibrosis, the method can survey a tissue sample identifying the cells or regions that are affected. After identifying the regions, the method can automatically compute the extent of fibrosis in the tissue sample. Similar qunatitative evaluation can be automated. For example, in the evaluation of chronic organ rejection the inflammatory process can be detected and its intensity graded.

Figure 3:
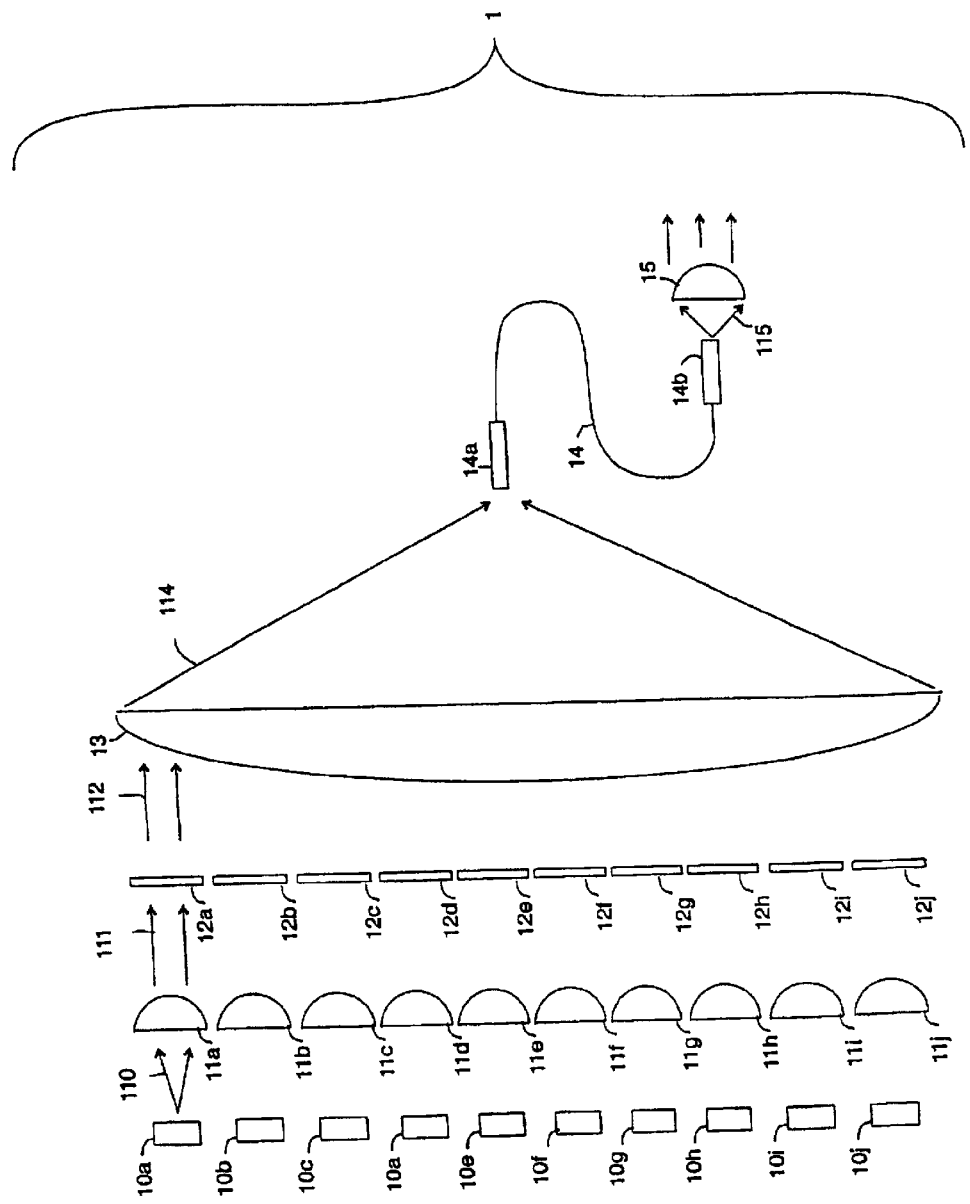
FIG. 3 shows a first implementation of the spectral illuminator.

We now describe specific implementations for the spectral illuminator. FIG. 3 shows a first implementation of a spectral illuminator 1. LED lamps 10a–j produce light 110 of various wavelengths that span the spectral range of interest (normally the photopic visible). Lenses 11a–j collimate the light from each LED to form light 111 and bandpass filters 12a–j provide spectral filtration of the various bands so that the light 112 has in each band a very well-defined spectral range with much greater specificity than that defined by the LEDs themselves. Objective 13 re-images the collimated light 114 from the various LED channels onto the tip 14a of optical fiber 14. When light emerges from this fiber end 14b, it is imaged by lens system 15 and directs light 115 towards the sample without spectro-spatial artifacts.

The illuminator in the FIG. 3 has ten spectral channels, but this is meant to be illustrative rather than restrictive, and systems may be built with any number of channels utilizing the same principles. The beam from each LED is collimated to produce a pupil plane at infinity, oriented parallel to a common optical axis z. The various LEDs and collimators are tiled at the entrance aperture of a telescope, which images all rays of a shared propagation direction to a common point. An optical fiber is placed at that point. The telescope causes the spatially distinct but parallel rays from the various LEDs to pass through a single point with various angles. The optical fiber randomizes the angular distribution, provided that its length is long enough that all rays undergo multiple reflections within it.

While a range of configurations are possible, most commonly the spectral channels will be in the range of 3 nm–20 nm per band, and there will be from 8 to 80 spectral bands overall. LEDs are not presently available with spectral widths narrower than about 35 nm, so it is normally necessary to use interference filters to further define the passband from each given LED. For example, in FIG. 3, there are 10 LEDs and interference filters with center wavelengths spanning the range 430 nm–655 nm by 25 nm intervals. Since the light is collimated at the point it passes through the bandpass filters, the spectral properties of those elements are not compromised.

The combination of the LED collimator lens and the telescope comprise a magnifier with gain F2/F1, where F2 is the focal length of the telescope and F1 is the focal length of the collimator lens. The design of this assembly presents optical engineering problems as will be known to one skilled in the art of optical design. Primary goals are to produce a high efficiency in coupling light from the LED into the fiber, and to ensure the design is manufacturable without requiring unduly tight dimensional tolerances.

Use of a large diameter optical fiber is often favored since this enables capturing more light. Similarly, use of optical fiber with relatively high numerical aperture (NA) is favored in many designs, since the fiber NA limits the effective NA of the telescope. Higher NA means a shorter telescope may be employed, to produce a more compact assembly.

Choice of particular LEDs is dictated by the need for spectral coverage and high brightness. The latter is important since the overall brightness of the illuminator is proportional to the spectral radiance of the LED. It is possible to use bare LEDs of the type that emit vertically (normal to the chip surface), as well as to use packaged LEDs. Choice of one over the other will be dictated by the properties of available LED sources, as well as cost, ease of assembly, and other practical factors. Suitable LEDs include high-brightness LEDs from Stanley Electric (London, Ohio), Cree Research (Durham, N.C.), Nichia (Tokushima, Japan), and KingBright (City of Industry, Calif.). These are sometimes hyperbolically described as "ultrabright", "superbright", and the like. Cree provides LEDs at 430, 450, 470, 490, 505, and 525 nm, which between them cover the range 420–540 nm. Many manufacturers provide LEDs covering the range 525–680 nm and the near-IR range, as is well-known in the art, and one source of such LEDs is MarkTech Optoelectronics (Menands N.Y.). When packaged LEDs can be used, the rays leaving the LED are refracted somewhat by the package, and it may be helpful in some cases to polish the LED front to be flat instead. The collimating lenses 11 a–j are designed accordingly with the goal of maximizing the energy that is coupled into the fiber.

In a related embodiment, the lenses 11 consist of 19 individual lenses, each with 25.4 mm focal length and diameter of 12.7 mm. They are tiled in a hexagonal close-packed arrangement within an overall diameter of 63.5 mm. Nineteen LEDs having wavelengths from 420–690 nm arranged by 15 nm intervals are situated behind the lenses, and nineteen interference filters having corresponding passbands are placed in front of the lenses. Mechanical mounting of the lenses and filters is accomplished using the space between the circles, so maximum packing density is achieved. The telescope consists of a lens with 65 mm diameter and 75 mm focal length, for a working N.A. of 0.397. It couples the collimated light from these LEDs into a 3M multimode fiber with 1 mm core and an NA of 0.39 (ThorLabs, Newton N.J., part FT-1.0-UMT). The fiber length is 2 meters, and at the distal end an achromatic lens of 25.4 mm focal length and 22 mm diameter images the fiber tip to infinity. The output beam may be directly coupled into microscopes such as the Zeiss AxioPlan (available from Carl Zeiss, Thornwood, N.Y.).

In many cases, it is preferable to use a lens array rather than individual lenses for each LED. The lenses can be plastic or glass, as long as the optical quality does not degrade the efficiency of optical coupling into the fiber. Mirrors may be used instead of lenses at each and every instance, and the choice of one over the other will be dictated by cost, optical performance, and other engineering design factors.

It is not essential in the design of FIG. 3 that all LEDs have the same size lens. Varying the numerical aperture (N.A.) of the LED collimation lens provides a means for adjusting the collection efficiency, and hence for tailoring the overall output of the system. Since different LEDs have different spectral radiance properties, this can be desirable. Adjustment of LED drive current is another means for balancing or tailoring the relative output powers of the various channels when each is set to its full-scale intensity setting.

Figure 4:
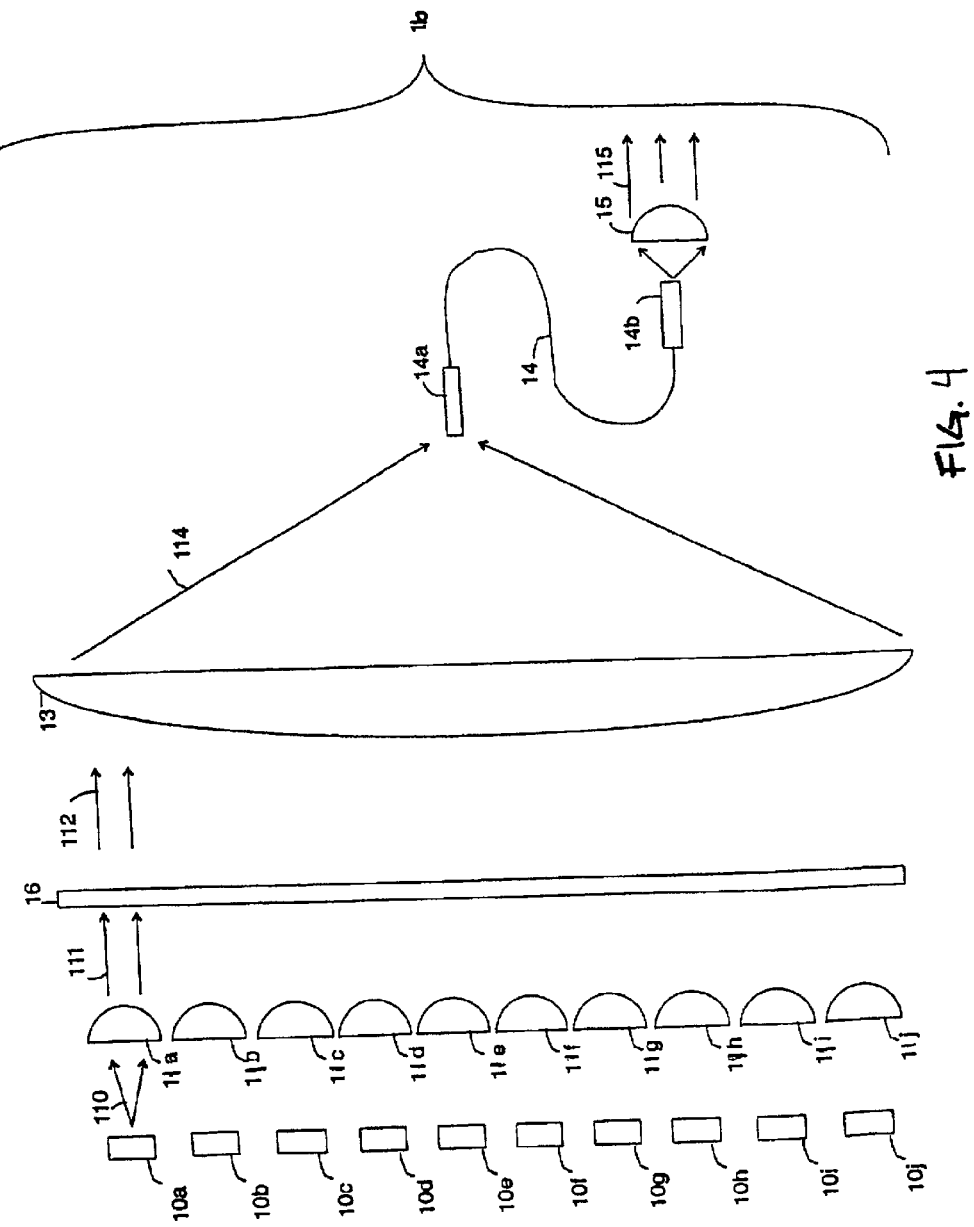
FIG. 4 shows another implementation of the spectral illuminator.
Figure 5:
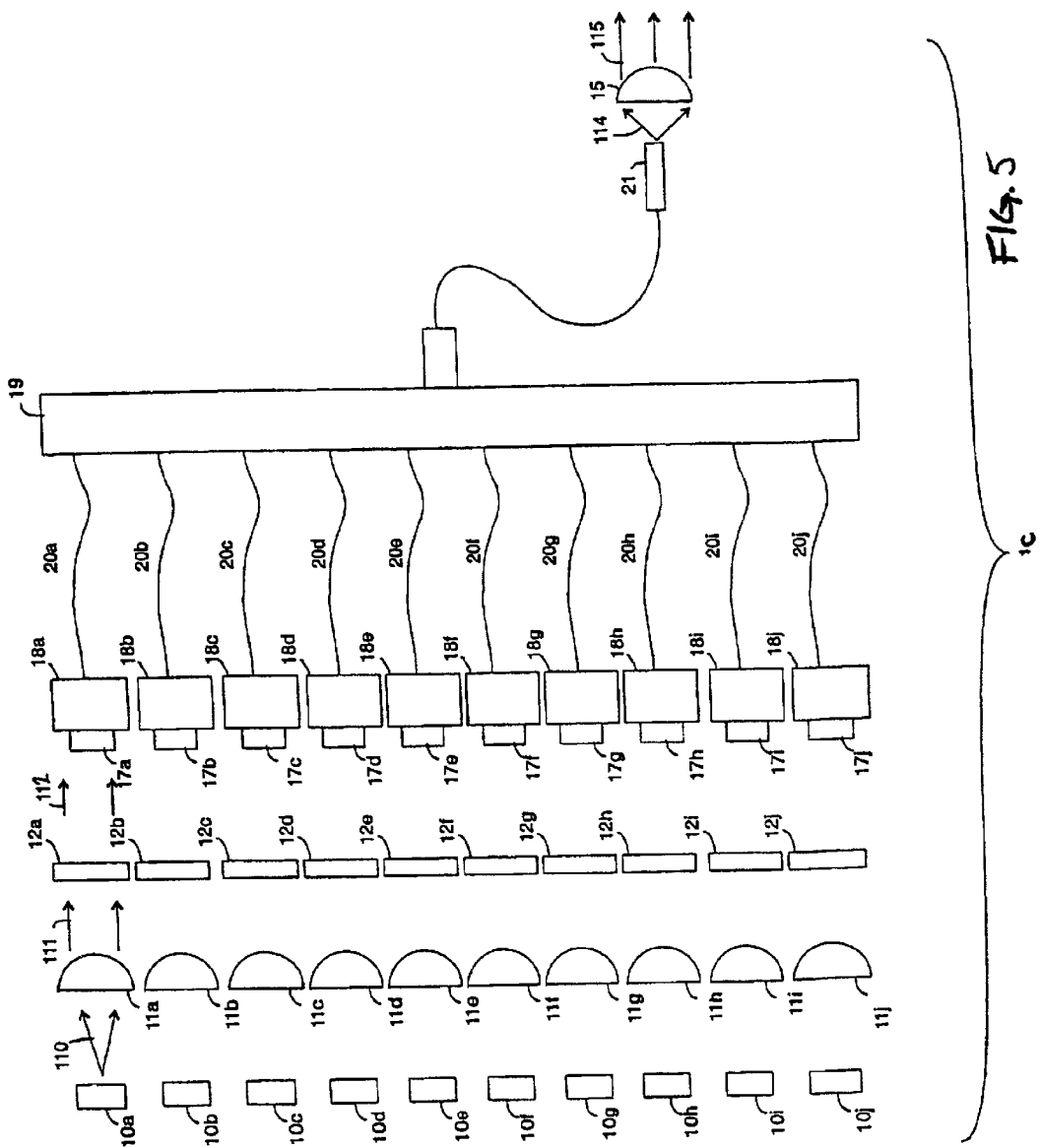
FIG. 5 shows another implementation of the spectral illuminator.

Referring to FIG. 4, a spectral illuminator 1b is shown. LED lamps 10a–j produce light 110 of various wavelengths that span the spectral range of interest (normally the photopic visible). Lenses 11a–j collimate the light from each LED to form light 111. The light passes through a linear-variable filter. These are available from OCLI (Santa Rosa, Calif.) or Reynard Coatings (Marina Del Rey, Calif.). The light 112 has in each band a very well-defined spectral range with much greater specificity than that defined by the LEDs themselves. Objective 13 re-images the collimated light 114 from the various LED channels onto the tip 14a of optical fiber 14. When light emerges from this fiber end 14b, it is imaged by lens system 15 and directs light 115 towards the sample without spectro-spatial artifacts.

In this arrangement, the lenses, while approximately spherical or aspherical in surface figure, may preferably have a rectangular shape with a longer axis transverse to the direction of the LED array. This enables better optical efficiency, since they can collect over a greater area.

It is possible to use other elements in concert with, or instead of, the optical components described above to couple the light from several LEDs into a single beam, and to homogenize the beam. Suitable elements include without limitation liquid-type light guides, or spatial scramblers comprising a tube-like enclosure whose internal surfaces are reflective. The latter can be constructed from a glass cylinder whose inner surface is silvered, or four strip-shaped first-surface mirrors arranged to form a rectangular cylinder, or a similar arrangement. In any case, the length of the tube should be several times the width of the tube, in order to sufficiently perform the function of the optical scrambling.

Figure 6:
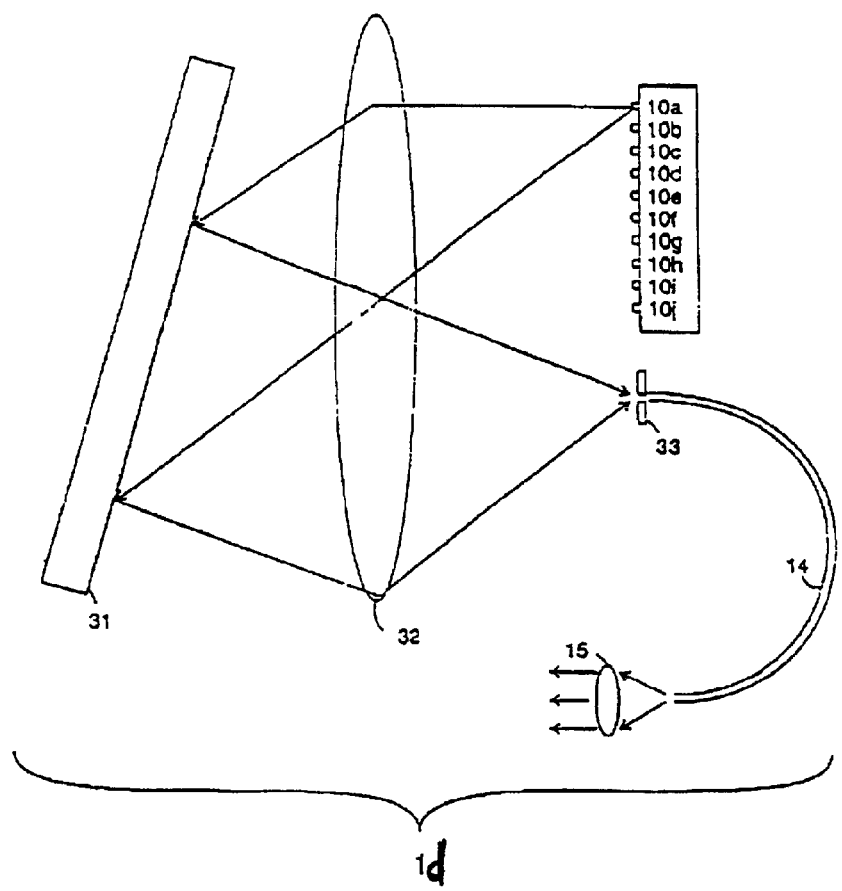
FIG. 6 shows another implementation of the spectral illuminator.

The use of fiber couplers to merge the various sources also eliminates or simplifies some of the alignment problems and enables a modular design, where each source (LED, collimating optics, and bandpass filter) is coupled into a fiberized connector, into which the fiber coupler inputs are plugged. Referring to FIG. 6, a related embodiment of this invention is shown. It is intended for fluorescence excitation uses. LED lamps 10a–j produce light 110 of various wavelengths that span the spectral range of interest (normally the photopic visible). Lenses 11a–j collimate the light from each LED to form light 111 and bandpass filters 12a–j provide spectral filtration of the various bands so that the light 112 has in each band a very well-defined spectral range with much greater specificity than that defined by the LEDs themselves. The light is then coupled into connectors 18a–j by coupling optics 17a–c. A fused fiber coupler 19 from Gould Fiber Optics (Millersville Md.) has input fibers 20a–j and output fiber tip 21. When light emerges from this fiber end 21, it is imaged by lens system 15 and directs light 115 towards the sample without spectro-spatial artifacts. The number of LED sources is M and the fiber coupler has N inputs. This enables use of N inputs at any one instant, under electronic control, in a few microseconds, with no moving parts. Each source can further be modulated in order to perform time-resolved measurements, as is known in the art.

If M equals N, then all bands are accessible at any time. However, this requires an M-fold fiber optic coupler, which becomes expensive for M greater than 2 or 4. While it is unusual for a given experiment to require more than 4 excitation bands, it is common that a researcher will require a wider range of spectral bands over the course of various experiments. This embodiment provides connectors for each LED source, into which a fiber can be inserted. This enables a user to select which of the M bands are of interest for a given experiment, and to plug the fiber coupler input into the appropriate bands. The arrangement is analogous to a telephone patch-bay, where plugging in to the proper jack may access various sources.

Further, the system exhibits greater optical efficiency compared to an arrangement which places all M sources in the pupil plane of the telescope, as the previous embodiments do, since it better utilizes the numerical aperture of the fiber into which the sources are coupled (or equivalently, of the numerical aperture of the telescope which merges their signals). Significantly, the instrument is instantly reconfigurable in the field by the customer without alignment problems. So it is practical to provide a wide array of source wavelengths, out of which only a few are selected for a given experiment, by means of the fiber-optic patch-bay.

FIG. 6 shows another implementation of a spectral illuminator Id where LED lamps 10a–j are placed at the focal plane of a spectrometer comprising reflective grating 31, lens system 32, and optional exit slit 33. Light emerging from the LEDs is spectrally selected by the grating according to the grating equation and the position of the LEDs, so that only a precisely regulated band enters multimode optical fiber 14 and passes to the sample through lens system 15.

Figure 7:
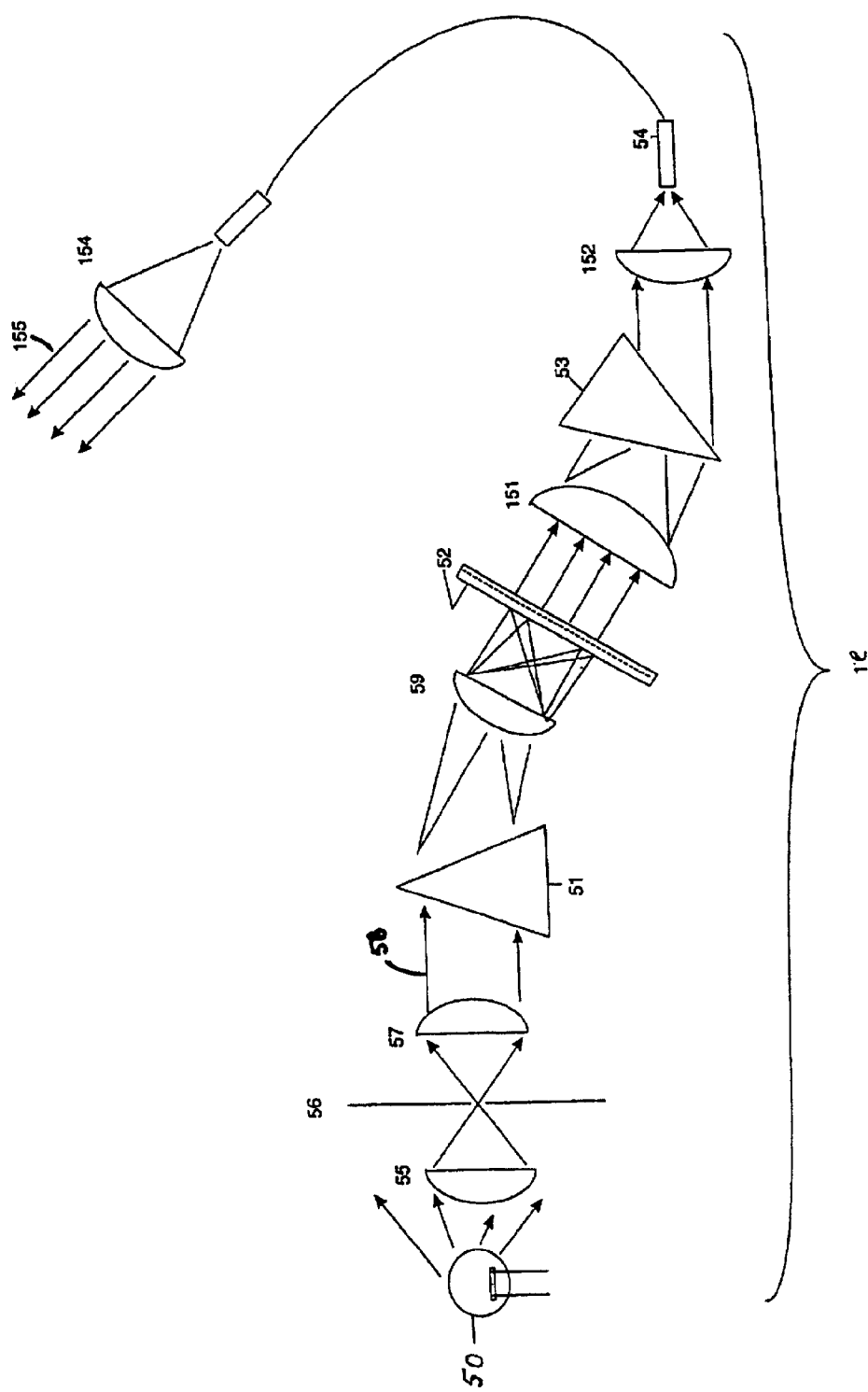
FIG. 7 shows another implementation of the spectral illuminator.

Another approach which may be used to realize a spectral illuminator is pictured in FIG. 7. A lamp 50 and lens 55 illuminate a slit 56 that is imaged to infinity by lens 57. Collimated rays 58 pass to prism 51 where they are dispersed according to wavelength and re-imaged by lens 59 to produce a spectrum at programmable mask 52. This element has a linear array of stripes arranged along an axis that is essentially parallel to the dispersion axis of the spectrum, where each stripe has an electrically variable transmission. Such an element can be constructed using a liquid crystal modulator, where each stripe is a single pixel with a transmission that is altered by the action of the liquid crystal material. These are commercially available from a number of manufacturers, including Cambridge Research and Instrumentation (Woburn, Mass.). The model SLM-128 amplitude mask with integral polarizers is one example of a suitable programmable mask, but any device that provides electrically variable transmission elements in a linear array is suitable. High peak transmission and a wide dynamic range of adjustment are key parameters for this device. Each stripe of the mask 52 controls the transmission for a selected spectral band, and by adjusting the mask it is possible to transmit all, none, or any precisely selected mixture of wavelengths. The light passing through 52 is re-collimated by lens 151 and passes through a second prism 53 that is oriented with its dispersion opposite to that of prism 51. Light emerges from prism 53 in a collimated state, and is re-imaged by lens 152 onto a linear fiber array 54. The fibers in this array are formed into a circular pattern at the other end, where lens 154 couples light 155 from the fibers towards the sample. Equivalent systems can be constructed using gratings in place of the prism elements 51 and 53. Other embodiments of the spectral illuminator can include using diffraction gratings, electronically tunable filters such as acousto-optic tunable filters (AOTFs) or liquid crystal tunable filters (LCTFs).

Figure 8:
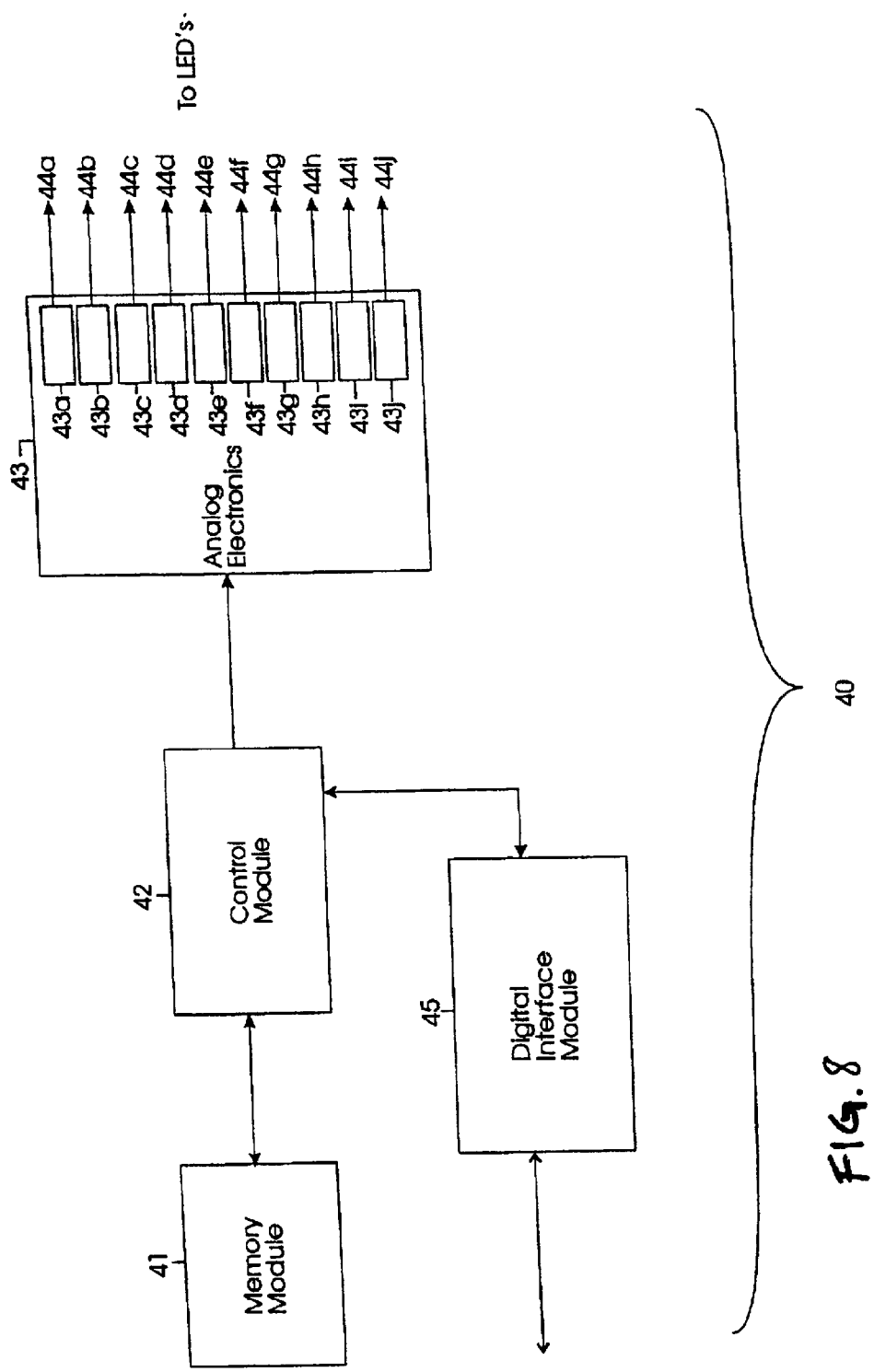
FIG. 8 shows a block diagram of the electronics used in the spectral illuminator.

The overall scheme of the electronics 40 is illustrated in FIG. 8, which shows a digital control module 42 that communicates with external control means via an interface 45 and generates signals 44a–44j by means of circuits 43a–43j. Optional digital storage element 41 contains drive information for one or more spectral weighting functions. When the spectral illuminator is used in conjunction with a detector of some kind that has linear response, it is possible to use the detector to calibrate the illuminator. This makes use of the linear detector response to generate an in-situ calibration of the possibly nonlinear illuminator.

Additional embodiments and details of suitable multi-spectral illuminators and multi-spectral illuminator systems are described in commonly owned U.S. utility application Ser. No. 10/163,233 by Paul J. Cronin et al., filed Jun. 4, 2002 and entitled "Multispectral Imaging System," the contents of which are incorporated herein by reference.

The use of medical examples is not meant to suggest that this is the sole or predominant use of the present invention. The method described is also suitable for the use of borescopes for industrial inspection, in reflected-light microscopy for semiconductor and materials measurements, and in any endeavor where spectral signatures enable discrimination between sample regions or quantification of sample properties. One such application is in the field of counterfeit detection, since in general the dyes, paints, and materials used in a counterfeit will not match the genuine article at all wavelengths even if the overall visual appearance is quite similar. A spectral weighting function that maximally illuminates in the spectral regions where the genuine article and the fake are different, will highlight these distinctions and make them readily apparent. The present invention provides a means for at once identifying the weighting function (through taking of a spectral image cube and its subsequent analysis on a computer), and then providing essentially real-time imaging of the objects using that derived spectral weighting function (by having the spectral illuminator provide the weighted illuminants while imaging the sample).

A number of embodiments of the invention have been described. Nevertheless, it will be understood that various modifications may be made without departing from the spirit and scope of the invention. Accordingly, other embodiments are within the scope of the following claims.

What is claimed is:

1. A method for imaging comprising:
   obtaining a spectral weighting function indicative of an attribute of a reference sample;
   illuminating a target sample with light whose spectral flux distribution corresponds to the spectral weighting function to produce a corresponding target image, wherein the target image is indicative of a response of the target sample to the corresponding illumination at multiple spatial locations of the target sample; and
   identifying one or more target features in the target sample based on the target image.

2. The method of claim 1 wherein
   the spectral weighting function is obtained from a set of reference images.

3. The method of claim 2 further comprising
   illuminating a reference sample at each of a plurality of pure spectral bands to produce the set of reference images, wherein each reference image is indicative of a response of the reference sample to the corresponding illumination at multiple spatial locations of the reference sample.

4. The method of claim 1, further comprising
   determining one or more additional spectral weighting functions indicative of additional attributes of the reference sample based on the set of reference images; and
   illuminating a target sample with light whose spectral flux distribution corresponds to each of the additional spectral weighting functions to produce additional corresponding target images, wherein each target image is indicative of a response of the target sample to the corresponding illumination at the multiple spatial locations of the target sample.

5. The method of claim 3, wherein the response of the reference sample comprises transmission, reflectance, or fluorescence.

6. The method of claim 1, wherein the response of the target sample comprises transmission, reflectance, or fluorescence.

7. The method of claim 1, wherein the spectral weighting function comprises multiple ones of the spectral bands.

8. The method of claim 1, wherein the spectral weighting function is a single one of the spectral bands.

9. The method of claim 2, wherein the spectral weighting function is determined based on at least one of principal component analysis, projection pursuit, independent component analysis, convex-hull analysis, and machine learning.

10. The method of claim 3, further comprising preparing the reference and target samples with markers suitable for chromogenic in-situ hybridization.

11. The method of claim 10, wherein the response of the target sample to the spectral weighting function correlates with the presence of the in-situ hybridization marker in the target sample.

12. The method of claim 3, further comprising preparing the reference and target samples with a marker suitable for color immunohistochemistry.

13. The method of claim 12, wherein the response of the target sample to the spectral weighting function correlates with the presence of the color immunohistochemistry marker in the target sample.

14. The method of claim 3, further comprising preparing the reference and target samples with a general stain.

15. The method of claim 1 wherein the identification includes assigning the one or more target features to one or more classes.

16. The method of claim 1 wherein the identification includes quantifying the amount of a chromogen in a target feature.

17. The method of claim 1, further comprising automating a subsequent process based on the identification of the one or more target features.

18. The method of claim 17, wherein the subsequent process includes laser capture microdissection.

19. The method of claim 18, wherein the laser capture microdissection includes directing laser energy to the identified target features in the target sample to remove corresponding portions of the target sample.

20. The method of claim 19, further comprising performing mass spectroscopy on the portions of the target sample removed by laser capture microdissection process.

21. The method of claim 20, wherein the mass spectroscopy is protein mass spectroscopy.

22. The method of claim 18, further comprising performing protein purification on the portions of the target sample removed by laser capture microdissection process.

23. The method of claim 17 wherein the subsequent process includes determining the extent of a condition or disease in a target sample.

24. The method of claim 23 wherein the condition is fibrosis.

25. The method of claim 23 wherein the condition is chronic organ rejection.

26. The method of claim 1, further comprising repetitively illuminating the target sample with light whose spectral flux distribution corresponds to the spectral weighting function to record the target image as a function of time.

27. The method of claim 26 wherein the identifying one or more target features is based on the time dependence of the target image.

* * * * *